US010874631B2

United States Patent
Mooberry et al.

(10) Patent No.: US 10,874,631 B2
(45) Date of Patent: Dec. 29, 2020

(54) ALTERTOXIN II AS A SELECTIVE INHIBITOR OF EWING FAMILY OF TUMOR CELLS

(71) Applicants: Susan L Mooberry, Austin, TX (US); Andrew J Robles, Austin, TX (US); April L Risinger, Austin, TX (US); Robert H Cichewicz, Norman, OK (US); Saikat Haldar, Norman, OK (US); Peter Houghton, Austin, TX (US)

(72) Inventors: Susan L Mooberry, Austin, TX (US); Andrew J Robles, Austin, TX (US); April L Risinger, Austin, TX (US); Robert H Cichewicz, Norman, OK (US); Saikat Haldar, Norman, OK (US); Peter Houghton, Austin, TX (US)

(73) Assignees: THE BOARD OF REGENTS OF THE UNIVERSITY OF TEXAS SYSTEM, Austin, TX (US); THE BOARD OF REGENTS OF THE UNIVERSITY OF OKLAHOMA, Norman, OK (US)

( * ) Notice: Subject to any disclaimer, the term of this patent is extended or adjusted under 35 U.S.C. 154(b) by 0 days.

(21) Appl. No.: 16/471,905

(22) PCT Filed: Dec. 20, 2017

(86) PCT No.: PCT/US2017/067585
§ 371 (c)(1),
(2) Date: Jun. 20, 2019

(87) PCT Pub. No.: WO2018/119069
PCT Pub. Date: Jun. 28, 2018

(65) Prior Publication Data
US 2020/0101038 A1 Apr. 2, 2020

Related U.S. Application Data

(60) Provisional application No. 62/437,333, filed on Dec. 21, 2016.

(51) Int. Cl.
*A61K 31/336* (2006.01)
*A61P 35/00* (2006.01)
*A61K 9/00* (2006.01)

(52) U.S. Cl.
CPC .......... *A61K 31/336* (2013.01); *A61K 9/0019* (2013.01); *A61P 35/00* (2018.01)

(58) Field of Classification Search
CPC ...... A61K 31/336; A61K 9/0019; A61P 35/00
See application file for complete search history.

(56) References Cited

U.S. PATENT DOCUMENTS

| 6,528,489 | B1 | 3/2003 | Papathanassiu |
| 2014/0205573 | A1 | 7/2014 | Kis et al. |
| 2015/0051260 | A1 | 2/2015 | Toretsky et al. |
| 2016/0151344 | A1 | 6/2016 | Huang |

OTHER PUBLICATIONS

Fleck, et al., "Alternaria Toxins: Altertoxin II Is a Much Stronger Mutagen and DNA Strand Breaking Mycotoxing Than Alternariol and Its Methyl Ether in Cultured Mammalian Cells," *Toxicology Letters*, 214(1); 27-32, 2012.
Fleck, et al., "Epoxide Reduction to an Alcohol: A Novel Metabolic Pathway for Perylene Quinone-Type Alternaria Mycotoxins in Mammalian Cells," *Chemical Research in Toxicology*, 27(2), 247-253, 2014.
Hradil, et al., "Phytotoxins from Alternaria Cassiae," *Phytochemistry*, 28(1); 73-75, 1989.
International Search Report and Written Opinion Issued in Corresponding PCT Application No. PCT/US2017/67585, dated Mar. 5, 2018.
May, et al., "The Ewing's Sarcoma EWS/FLI-1 Fusion Gene Encodes a More Potent Transcriptional Activator and Is a More Powerful Transforming Gene Than FLI-1," *Molecular and Cellular Biology*, 13(12);7393-7398, 1993.
May, et al., "Ewing Sarcoma 11;22 Translocation Produces a Chimeric Transcription Factor That Requires the DNA-Binding Domain Encoded by FLI1 for Transformation," *PNAS*, 90, 5752-5756, 1993.
Schwarz, et al., "Characterization of a Genotoxic Impact Compound in Alternaria Alternata Infested Rice as Altertoxin II," *Archives of Toxicology*, 86(12); 1911-1925, 2012.
Stack, et al., "Mutagenic Perylenequinone Metabolites of Alternaria Alternata: Altertoxins I, II, and III," *Journal of Natural Products*, 49(5); 866-871, 1986.

*Primary Examiner* — Yong S. Chong
(74) *Attorney, Agent, or Firm* — Norton Rose Fulbright US LLP

(57) ABSTRACT

Certain embodiments are directed to methods for treating Ewing family tumors (EFT) comprising administering an effective amount of altertoxin II to a subject having EFT.

10 Claims, 9 Drawing Sheets

| Position | $\delta_H$ mult. ($J$) ($d_6$-Me$_2$CO) | $\delta_C$ ($d_6$-DMSO) |
| --- | --- | --- |
| 1 | 8.14 d (8.7) | 132.98[a] |
| 2 | 7.06 d (8.7) | 118.04[c] |
| 3 | - | 161.22[b] |
| 3a | - | 113.68[d] |
| 4 | - | 205.57 |
| 5 | 3.25 m, 2.97 m | 32.99[e] |
| 6 | 2.76 m, 2.60 m | 31.99[e] |
| 6a | - | 67.15 |
| 6b | 3.63 s | 44.11 |
| 7 | 4.44 d (3.4) | 56.24 |
| 8 | 3.72 d (3.3) | 52.61 |
| 9 | - | 197.57 |
| 9a | - | 113.93[d] |
| 9b | - | 136.16 |
| 10 | - | 161.57[b] |
| 11 | 6.99 d (8.6) | 116.13[c] |
| 12 | 8.05 d (8.7) | 133.16[a] |
| 12a | - | 124.47 |
| 12b | - | 122.87 |
| 12c | - | 140.47 |
| 3-OH | 12.79 s | - |
| 10-OH | 12.08 s | - |
| 6a-OH | 3.31 s | - |

[a-e] Assignments may be interchanged.

LC-MS ESI(-) *m/z*: [M-H]⁻ Calcd 349.08, found 349.10

[α]$^{25}_D$ +693 (*c* 0.124, MeOH)   [Reported: [α]$_D$ +636 (*c* 0.0.001, CHCl$_3$); *Reference #3*]

ALTERTOXIN II AS A SELECTIVE INHIBITOR OF EWING FAMILY OF TUMOR CELLS

PRIORITY PARAGRAPH

This application is a national phase application under 35 U.S.C. § 371 of International Application No. PCT/US2017/067585, filed Dec. 20, 2017 which claims priority to U.S. Provisional Patent Application Ser. No. 62/437,333 filed Dec. 21, 2016, each of which is incorporated herein by reference in its entirety.

FEDERAL FUNDING

This invention was made with government support under grant number GM107490 awarded by the National Institutes of Health. The government has certain rights in the invention.

BACKGROUND

This invention relates to the fields of medicine and pharmaceuticals. In particular, the invention relates to the identification of altertoxin II for use in inhibiting cell proliferation and disrupting cellular processes leading to cell death of Ewing family tumors.

Ewing sarcoma, and tumors of the closely related Ewing family of tumors, defined here as EFT, are aggressive and highly metastatic malignancies. EFT arises in and around the bones of the extremities and central skeleton, but may also arise in the soft tissues. EFTs primarily affect children and young adults, predominantly those of European descent, with the highest rates of development occurring in white male adolescents.

Cells of EFTs appear as small, round, undifferentiated blue cells upon H&E staining, and thus belongs to a class of tumors with a similar histologic appearance which includes rhabdomyosarcoma, neuroblastoma, and lymphoma. However, the cellular origin of EFT is unknown. Most cases of EFT emanate via a recurrent chromosomal translocation that encodes for the EWS/FLI1 fusion protein or a closely related variant. (See Delattre et al., *Nature,* 359, 162-65 (1992)). The FLI1 portion contains an ETS family DNA-binding domain while the EWS portion functions as a strong transcriptional activation domain. Accordingly, EWS/FLI1 is an aberrant transcription factor that dysregulates genes involved in tumor development (May et al., *Proc Natl Acad Sci USA,* 90, 5752-56 (1993a); May et al., *Mol Cell Biol,* 13, 7393-98 (1993b)).

There remains a need for additional compositions and methods for treating EFT.

SUMMARY

Certain embodiments are directed to methods for treating EFT comprising administering an effective amount of altertoxin II to a subject having EFT.

As used herein, the term "effective amount" or "pharmaceutically effective amount" or "therapeutically effective amount" of a composition, is a quantity sufficient to achieve a desired therapeutic and/or prophylactic effect, e.g., an amount which results in the prevention of, or a decrease in, the symptoms associated with a disease that is being treated. The amount of a composition administered to the subject will depend on the type and severity of the disease and on the characteristics of the individual, such as general health, age, sex, body weight, and tolerance to drugs. It will also depend on the degree, severity and type of disease. The skilled artisan will be able to determine appropriate dosages depending on these and other factors. The compositions can also be administered in combination with one or more additional therapeutic compounds.

As used herein, the term "subject" refers to a mammal, such as a human, but can also be another animal such as a domestic animal (e.g., a dog, cat, or the like), a farm animal (e.g., a cow, a sheep, a pig, a horse, or the like), or a laboratory animal (e.g., a monkey, a rat, a mouse, a rabbit, a guinea pig, or the like). The term "patient" refers to a "subject" who is, or is suspected to be, afflicted with EFT.

As used herein, the term "simultaneous" therapeutic use refers to the administration of at least two active ingredients by the same route and at the same time or at substantially the same time.

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for a disorder if, after receiving a therapeutic agent according to the methods of the present disclosure, the subject shows observable and/or measurable reduction in or absence of one or more signs and symptoms of a particular disease or condition.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE FIGURES

The following drawings form part of the present specification and are included to further demonstrate certain aspects of the present invention. The invention may be better understood by reference to one or more of these drawings in combination with the detailed description of the specification embodiments presented herein.

Figure 1:
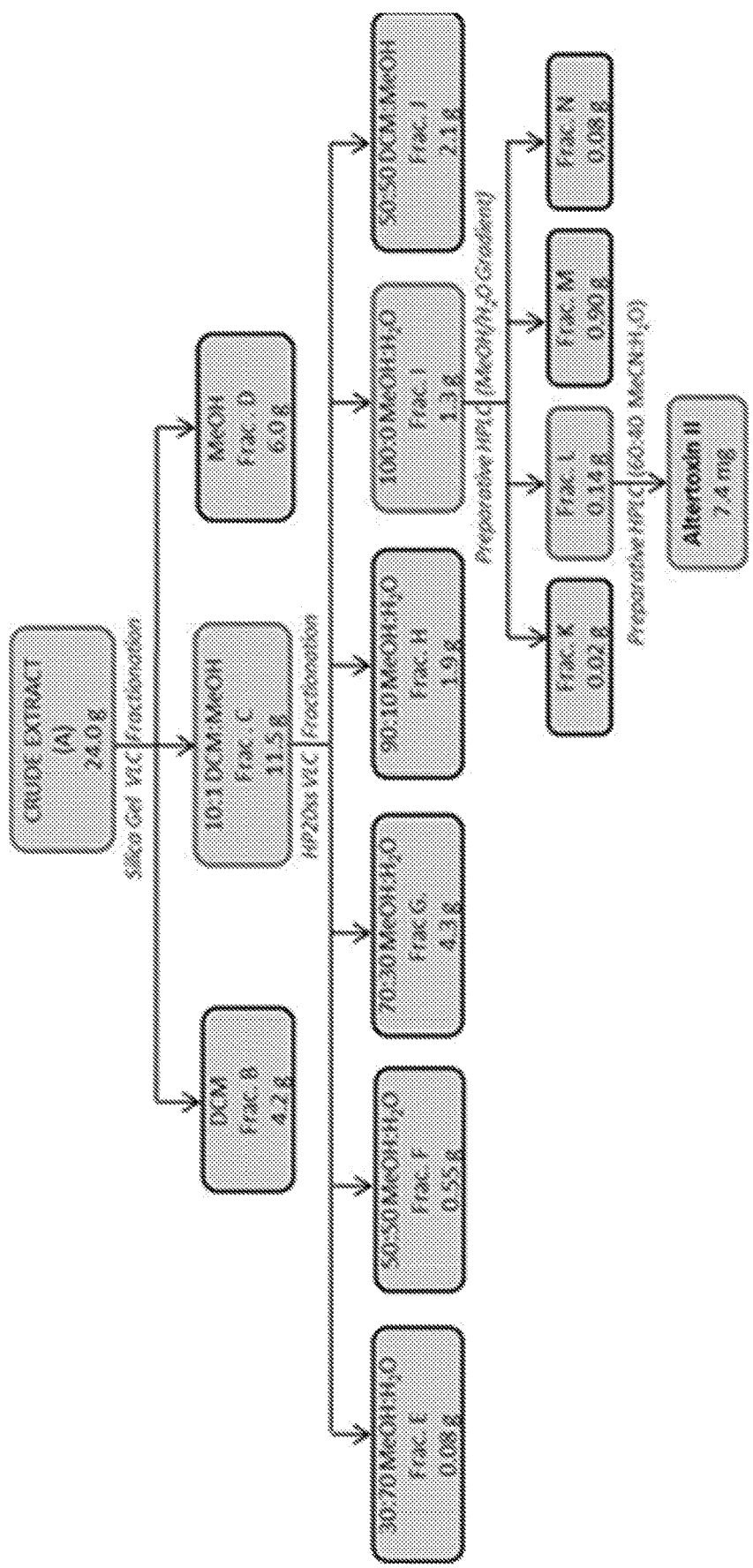

FIG. 1. Isolation scheme for altertoxin II. Fractions A, C, I, and L possess the highest cytotoxicity among all the related sub-fractions at every step. [Abbreviations: DCM, Dichloromethane; VLC, Vacuum Liquid Chromatography; Frac., Fraction]

Figure 2:
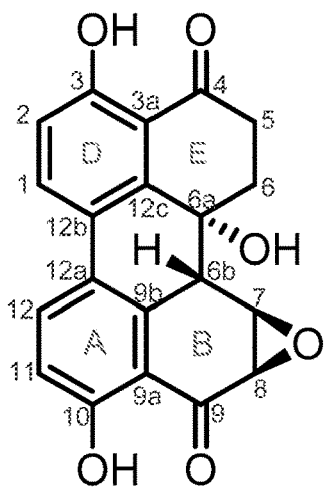

FIG. 2. $^1$H (400 MHz) and $^{13}$C NMR (100 MHz) data of altertoxin II

Figures 3A, 3B:
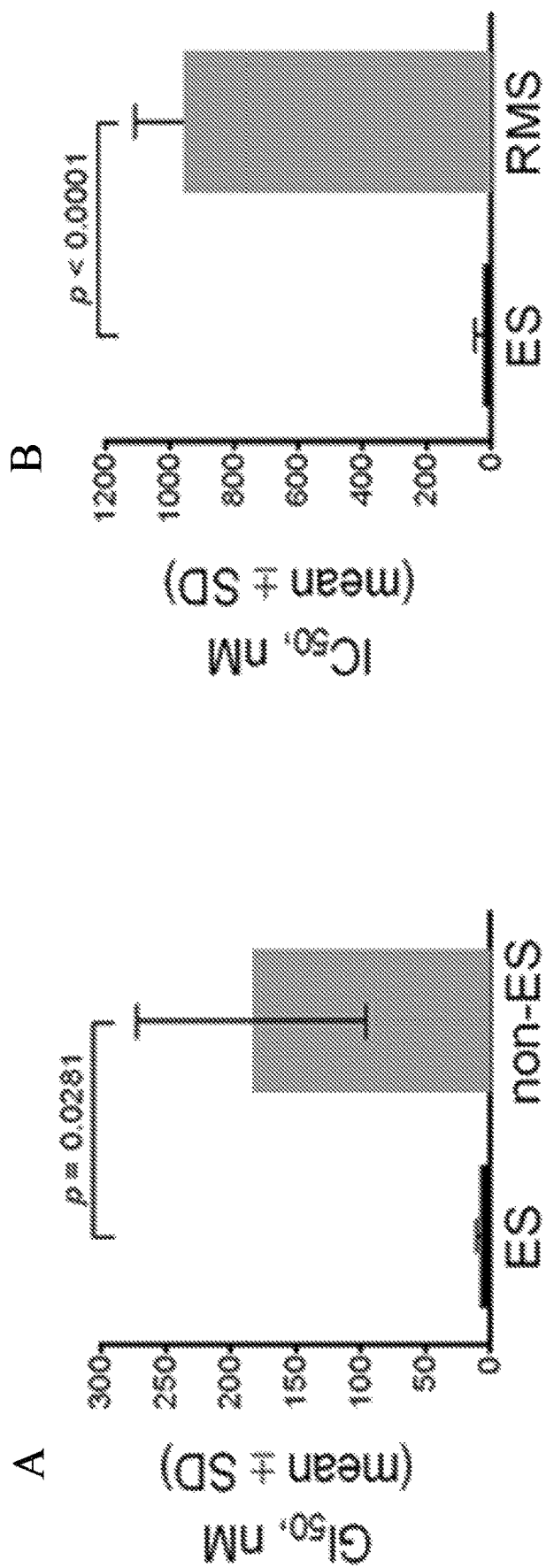

FIG. 3A-3B. (A) The effects of altertoxin II were evaluated using the SRB assay in 6 Ewing sarcoma cell lines as compared to 4 other pediatric solid tumor cells lines. n≥3 independent experiments. (B) The effects of altertoxin II were evaluated by the Houghton laboratory using the alamar blue assay in an additional 6 Ewing sarcoma cell lines and potency compared to the activities in 5 rhabdomyosarcoma cell lines. n=3 independent experiments.

Figure 4A:
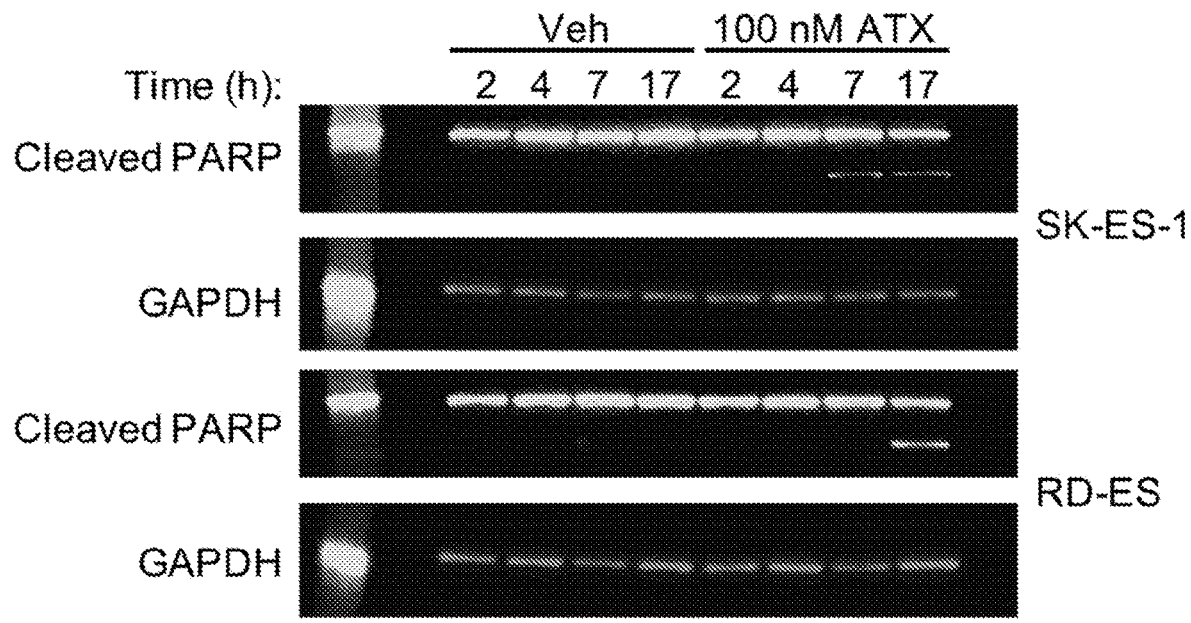
Figure 4B:
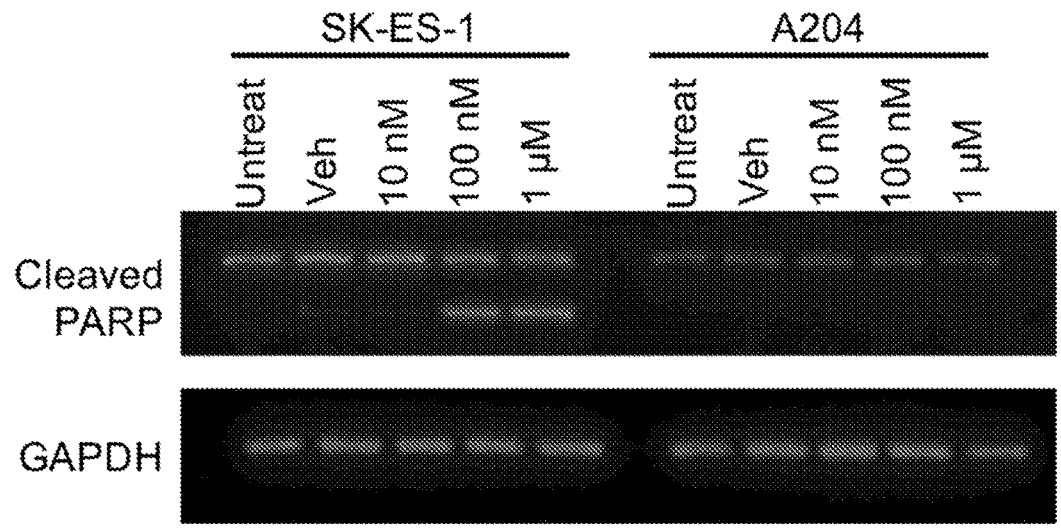

FIG. 4A-4B. Altertoxin II selectively induces PARP cleavage in EWS cell lines. Immunoblotting for total and cleaved PARP. (A) Two Ewing sarcoma (EWS) cell lines, RD-ES and SK-ES-1, were treated with 100 nM altertoxin II (ATX) for the indicated amounts of time. Whole-cell lysates were prepared and separated by SDS-PAGE. (B) The EWS cell line SK-ES-1 and rhabdomyosarcoma cell line A204 were treated with the indicated concentrations of ATX for 18 hours, lysed and separated by SDS-PAGE.

Figures 5A, 5B:
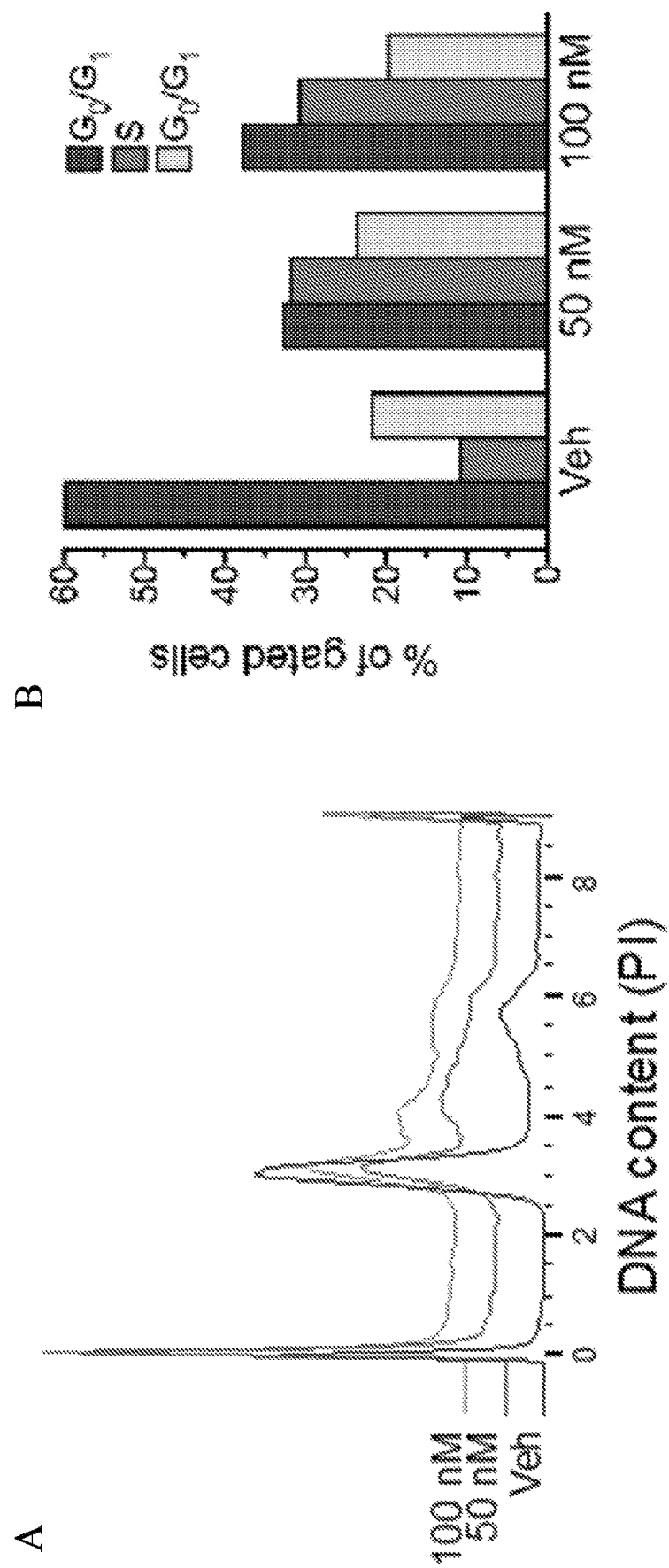

FIG. 5A-5B. Altertoxin II causes accumulation of SK-ES-1 Ewing sarcoma cells in the S-phase of the cell cycle. Cell cycle analysis of SK-ES-1 cells by flow cytometry. (A) Histogram of DNA content after treatment with two different concentrations of ATX for 18 hours. (B) quantification of cells in each cell cycle phase.

Figure 6:
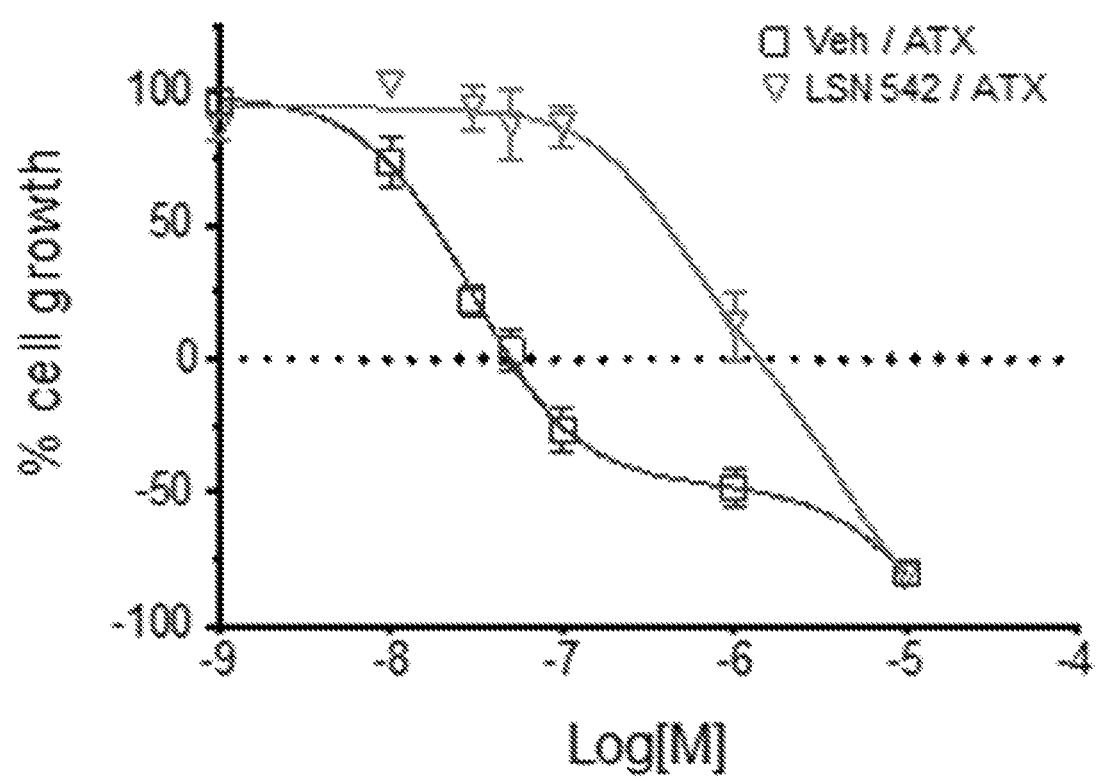

FIG. 6. Concentration-response curves for altertoxin II (ATX) with and without pre-treatment with the CDK4/6 inhibitor LSN2813542 (100 nM) using the SRB assay, n=3.

Figures 7A, 7B:
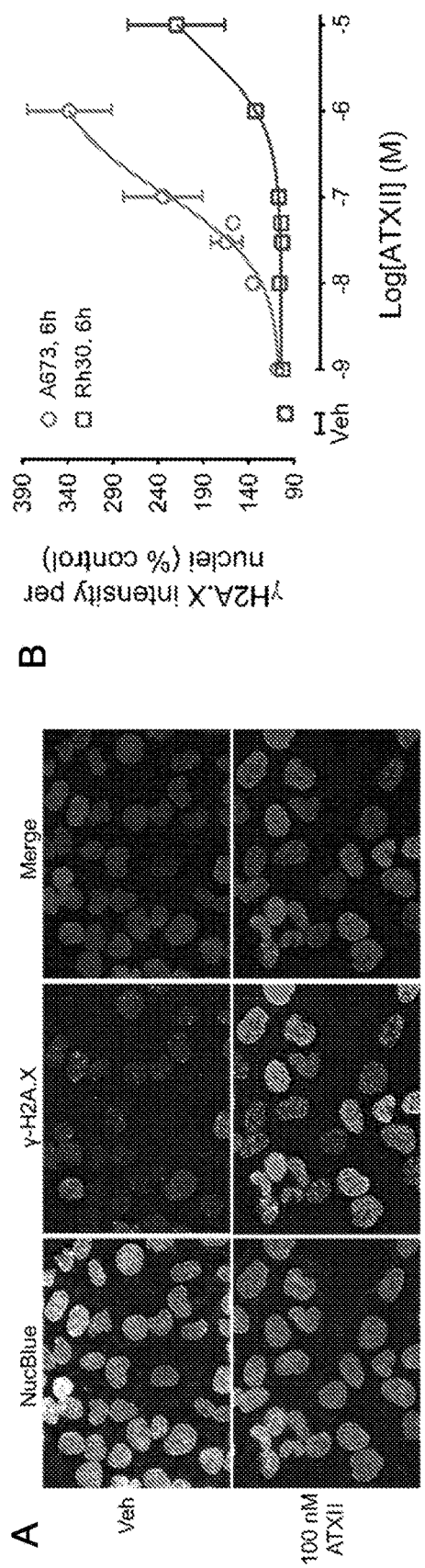

FIG. 7A-7B. Altertoxin II (ATXII) selectively induces γH2AX foci in A673 Ewing sarcoma cells. (A) A673 cells were treated for 24 h with 100 nM altertoxin II and serine 139 phosphorylation of γH2AX evaluated by indirect immunofluorescence techniques. (B) High-content imaging and image analysis were used to construct concentration-response curves for nuclear γH2AX intensity in A673 and Rh30 rhabdomyosarcoma cells after treatment with altertoxin II for 6 h.

Figures 8A, 8B:
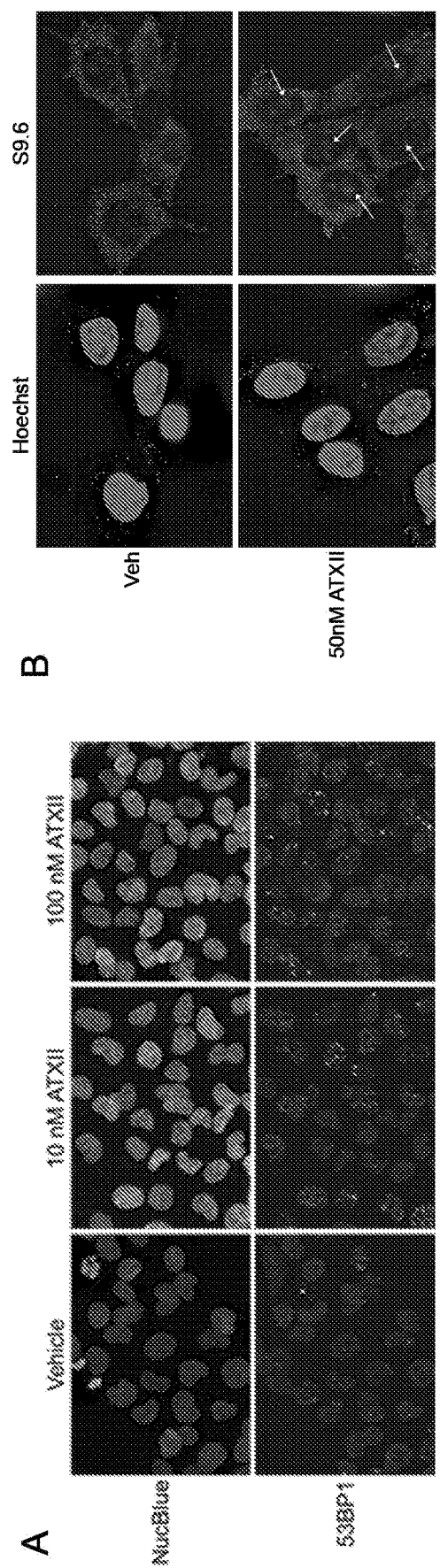

FIG. 8A-8B. The effects of 10 and 100 nM altertoxin II (ATXII) on 53BP1 foci were evaluated following a 6 h treatment of A673 cells by indirect immunofluorescence. (B) Immunofluorescence of R-loop marker S9.6 in TC-32 cells 24 h after ATXII treatment. Arrows indicate R-loops within nuclei.

Figure 9A:
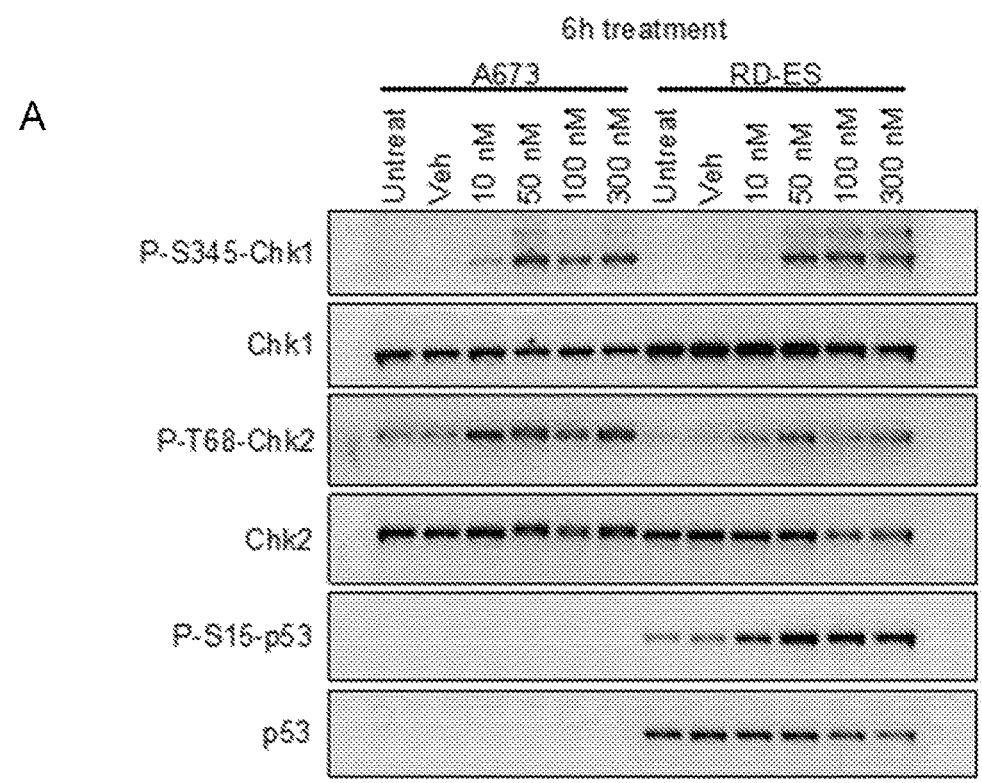
Figure 9B:
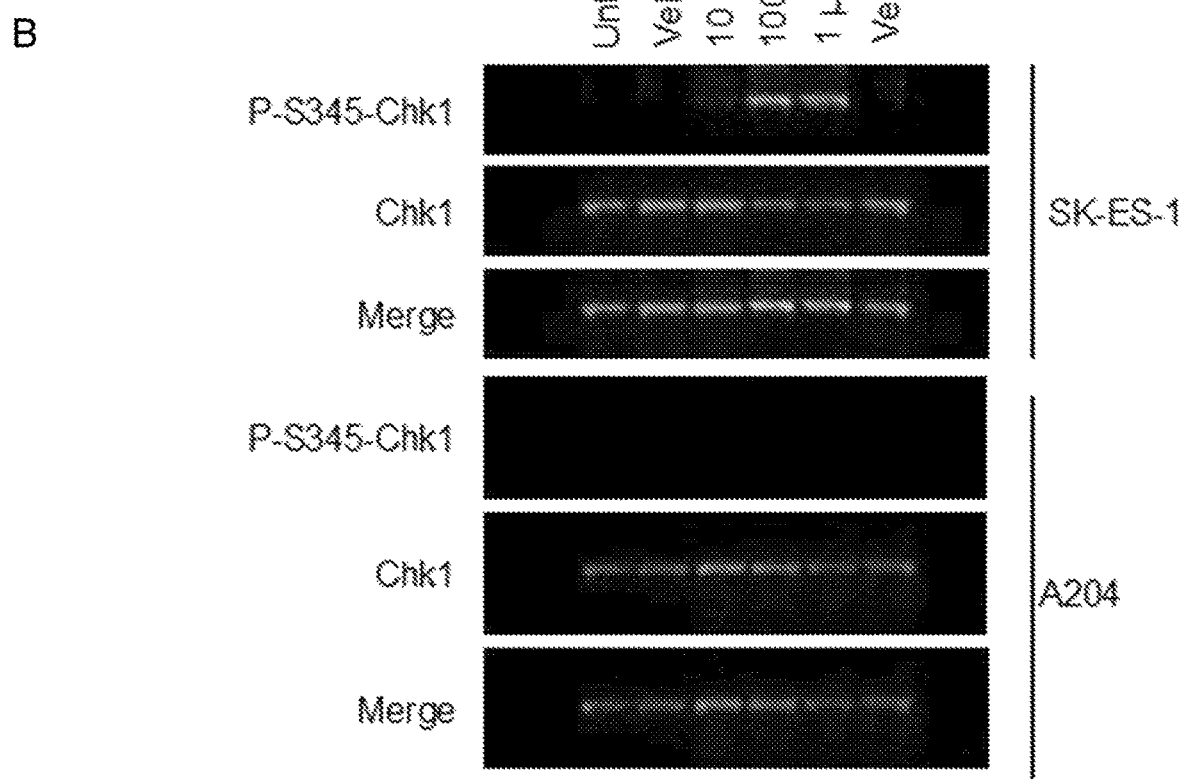

FIG. 9A-9B. Altertoxin II causes phosphorylation of CHK1 and 2 and p53 in Ewing sarcoma cells. Ewing sarcoma cells, A673, RD-ES, SK-ES-1, or rhabdomyosarcoma A204 cells were treated with altertoxin II at the concentrations indicated for 6 h (A) or 24 h (B) and whole-cell lysates prepared and proteins separated by SDS-PAGE. These samples were analyzed by immunoblotting for total and phosphorylated Chk1 and 2 and p53 (A).

Figure 10:
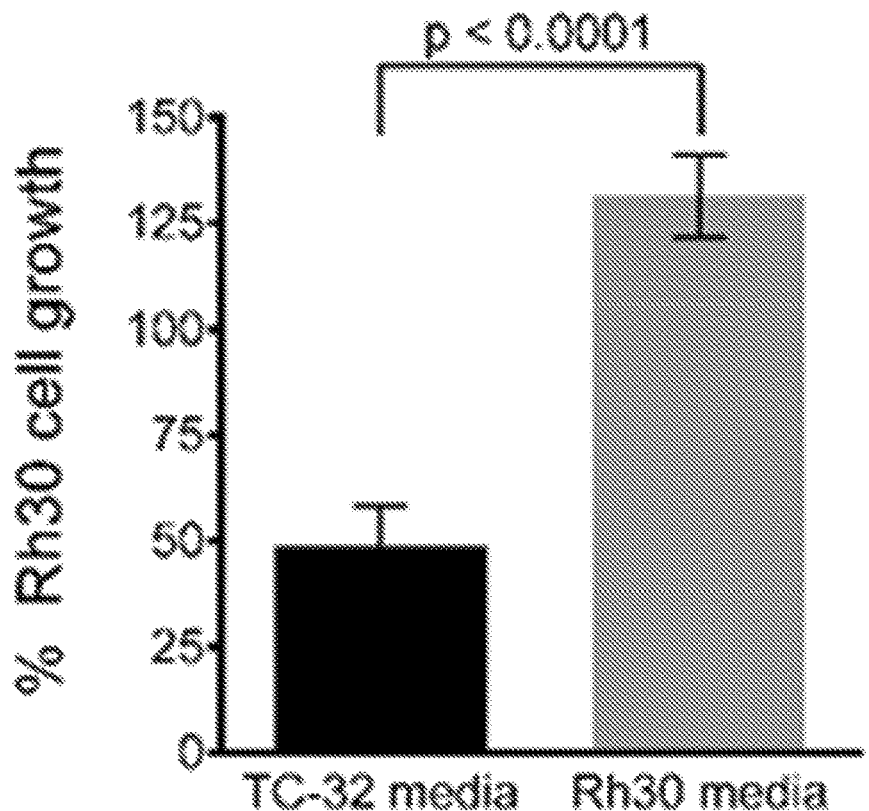

FIG. 10. Effects of ATXII-conditioned media on Rh30 cell growth. TC-32 or Rh30 cells were treated with 100 nM ATXII for 6 h, the media added to Rh30 cells and cell growth determined with the SRB assay.

Figure 11:
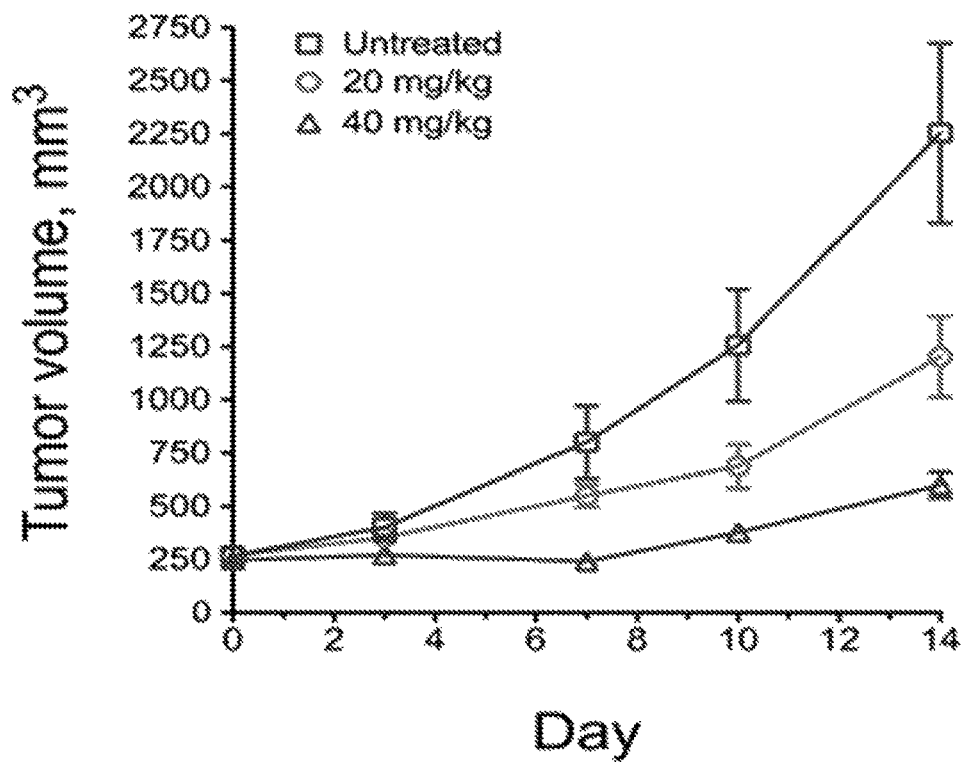

FIG. 11. Antitumor efficacy of ATXII against A673 xenograft model. Mice were injected i.p. with 20 mg/kg. ATXII on days 1, 3, 5, 8, 10 and 12, or 40 mg/kg on days 1, 3, and 5.

DESCRIPTION

Altertoxin II is a fungal metabolite with highly potent and selective activity against cell line models of Ewing Sarcoma. Growth of these cancer cells and EFT cells are driven by expression of the EWS-FLI1 fusion protein or a closely related fusion protein. Altertoxin II has selective activity against cell lines expressing these fusion proteins. In certain aspects of the invention altertoxin II can be an effective treatment for EFTs.

In certain embodiments, the invention also provides compositions comprising altertoxin II, and optionally, 1, 2, 3 or more anti-cancer agents with one or more of the following: a pharmaceutically acceptable diluent; a carrier; a solubilizer; an emulsifier; and/or a preservative. Such compositions may contain an effective amount of at least one anti-cancer agent, such as altertoxin II. Thus, the use of one or more anti-cancer agents that are provided herein in the preparation of a pharmaceutical composition of a medicament is also included. In certain embodiments the treatment is for EFT.

The anti-cancer agents may be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form depends upon the mode of administration and the particular disease targeted. The compositions also preferably include pharmaceutically acceptable vehicles, carriers, or adjuvants, well known in the art.

Acceptable formulation components for pharmaceutical preparations are nontoxic to recipients at the dosages and concentrations employed. In addition to the anti-cancer agents that are provided, compositions may contain components for modifying, maintaining, or preserving, for example, the pH, osmolarity, viscosity, clarity, color, isotonicity, odor, sterility, stability, rate of dissolution or release, adsorption, or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (see *Remington's Pharmaceutical Sciences,* 18 th Ed., (A. R. Gennaro, ed.), 1990, Mack Publishing Company), hereby incorporated by reference.

The compound of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo to the parent compound.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5-8.5, or acetate buffer of about pH 4.0-5.5, which may further include sorbitol or a suitable substitute therefor.

The pharmaceutical composition to be used for in vivo administration is typically sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

The above compositions can be administered using conventional modes of delivery including, but not limited to, intravenous, intraperitoneal, oral, intralymphatic, subcutaneous administration, intraarterial, intramuscular, intrapleural, intrathecal, and by perfusion through a regional catheter. Local administration to a tumor in question is also contemplated by the present invention. When administering the compositions by injection, the administration may be by continuous infusion or by single or multiple boluses. For parenteral administration, the anti-metastatic agents may be administered in a pyrogen-free, parenterally acceptable aqueous solution comprising the desired anti-cancer agents in a pharmaceutically acceptable vehicle. A particularly suitable vehicle for parenteral injection is sterile distilled water in which one or more anti-cancer agents are formulated as a sterile, isotonic solution, properly preserved.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

If desired, stabilizers that are conventionally employed in pharmaceutical compositions, such as sucrose, trehalose, or glycine, may be used. Typically, such stabilizers will be added in minor amounts ranging from, for example, about 0.1% to about 0.5% (w/v). Surfactant stabilizers, such as TWEEN®-20 or TWEEN®-80 (ICI Americas, Inc., Bridgewater, N.J., USA), may also be added in conventional amounts.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents. Compositions for parental administration are also sterile, substantially isotonic and made under GMP conditions.

For the compounds of the present invention, alone or as part of a pharmaceutical composition, such doses are between about 0.001, 0.01, 0.10, 1.0 mg/kg and 10, 20, 50 mg/kg body weight, preferably between about 1, 10, 50 and 75, 80, 100 µg/kg body weight, most preferably between 1 and 10 µg/kg body weight. Therapeutically effective doses will be easily determined by one of skill in the art and will depend on the severity and course of the disease, the subject's health and response to treatment, the subject's age, weight, height, sex, previous medical history and the judgment of the treating physician.

In liquid and semi-solid formulations, a concentration of a therapeutic compound disclosed herein typically may be between about 50 mg/mL to about 1,000 mg/mL. In aspects of this embodiment, a therapeutically effective amount of a therapeutic compound disclosed herein may be from, e.g., about 50 mg/mL to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 50 mg/mL to about 700 mg/mL, about 50 mg/mL to about 800 mg/mL, about 50 mg/mL to about 900 mg/mL, about 50 mg/mL to about 1,000 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 100 mg/mL to about 700 mg/mL, about 100 mg/mL to about 800 mg/mL, about 100 mg/mL to about 900 mg/mL, about 100 mg/mL to about 1,000 mg/mL, about 200 mg/mL to about 300 mg/mL, about 200 mg/mL to about 400 mg/mL, about 200 mg/mL to about 500 mg/mL, about 200 mg/mL to about 600 mg/mL, about 200 mg/mL to about 700 mg/mL, about 200 mg/mL to about 800 mg/mL, about 200 mg/mL to about 900 mg/mL, about 200 mg/mL to about 1,000 mg/mL, about 300 mg/mL to about 400 mg/mL, about 300 mg/mL to about 500 mg/mL, about 300 mg/mL to about 600 mg/mL, about 300 mg/mL to about 700 mg/mL, about 300 mg/mL to about 800 mg/mL, about 300 mg/mL to about 900 mg/mL, about 300 mg/mL to about 1,000 mg/mL, about 400 mg/mL to about 500 mg/mL, about 400 mg/mL to about 600 mg/mL, about 400 mg/mL to about 700 mg/mL, about 400 mg/mL to about 800 mg/mL, about 400 mg/mL to about 900 mg/mL, about 400 mg/mL to about 1,000 mg/mL, about 500 mg/mL to about 600 mg/mL, about 500 mg/mL to about 700 mg/mL, about 500 mg/mL to about 800 mg/mL, about 500 mg/mL to about 900 mg/mL, about 500 mg/mL to about 1,000 mg/mL, about 600 mg/mL to about 700 mg/mL, about 600 mg/mL to about 800 mg/mL, about 600 mg/mL to about 900 mg/mL, or about 600 mg/mL to about 1,000 mg/mL.

In solid formulations, a therapeutic compound disclosed herein typically may be present in a dose or in an amount between about 1 mg to about 500 mg. In aspects of this embodiment, a therapeutically effective amount of a therapeutic compound disclosed herein may be from, e.g., about 1 mg to about 100 mg, about 1 mg to about 200 mg, about 1 mg to about 300 mg, about 1 mg to about 400 mg, about 50 mg to about 200 mg, about 50 mg to about 300 mg, about 50 mg to about 400 mg, about 50 mg to about 500 mg, about 100 mg to about 300 mg, about 100 mg to about 400 mg, about 100 mg to about 500 mg.

In some methods of the invention, the cancer cell is a tumor cell. The cancer cell may be in a patient. The patient may have a solid tumor. In such cases, embodiments may further involve performing surgery on the patient, such as by resecting all or part of the tumor. Compositions may be administered to the patient before, after, or at the same time as surgery. In additional embodiments, patients may also be administered directly, endoscopically, intratracheally, intratumorally, intravenously, intralesionally, intramuscularly, intraperitoneally, regionally, percutaneously, topically, intrarterially, intravesically, or subcutaneously. Therapeutic compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

Methods of treating cancer may further include administering to the patient chemotherapy or radiotherapy, which may be administered more than one time. Chemotherapy includes, but is not limited to, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), docetaxel, paclitaxel, 5-fluorouracil, vincristine, vinblastine, eribulin, methotrexate, gemcitabine, oxaliplatin, irinotecan, topotecan, temozolamide, olaparib, or any analog or derivative variant thereof. Radiation therapy includes, but is not limited to, X-ray irradiation, UV-irradiation, gamma-irradiation, electron-beam radiation, or microwaves. Moreover, a cell or a patient may be administered a microtubule binding agent, including, but not limited to, a vinca alkaloid, eribulin or a taxane, as part of methods of the invention. It is specifically contemplated that any of the compounds or derivatives or analogs, can be used with these combination therapies.

Altertoxin II and two related compounds altertoxin I and alteichin were isolated from an *Alternaria* sp. fungal extract that had selective activity for Ewing sarcoma cells as compared to other adult and pediatric cancer cell lines. These three compounds were evaluated in a panel of 5 pediatric cancer cell lines representing 5 different types of solid pediatric cancers and the potent, Ewing sarcoma-specific effects of altertoxin II were confirmed. These results demonstrate initial structure-activity relationships (SAR), and the importance of the epoxide for the potent and Ewing sarcoma-selective activity of altertoxin II. Altertoxin I, which differs from altertoxin II only in terms of the epoxide, did not show selective cytotoxic activity against Ewing sarcoma cells.

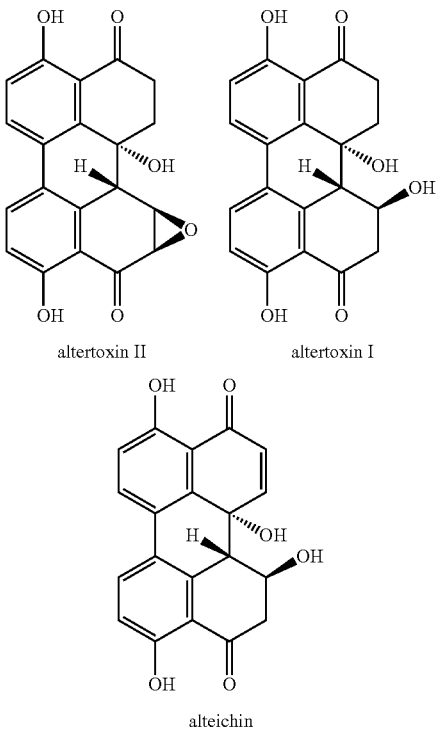

altertoxin II altertoxin I alteichin

The effects of altertoxin II were studied in a larger panel of cell lines and the $GI_{50}$, the concentration that causes 50% inhibition of cell growth, and the TGI, the concentration that caused total growth inhibition, were determined using the sulforhodamine b (SRB assay). These values are presented in Table 1. The mean $GI_{50}$ values shown graphically in FIG. 3A. The $IC_{50}$, the concentration that causes 50% inhibition of cell proliferation, values were determined in a second panel of Ewing sarcoma and rhabdomyosarcoma cell lines using the altar blue assay and these values are presented in Table 2 and the mean in FIG. 2B. These result show that every Ewing sarcoma cell line evaluated was extremely sensitive, with 58-fold selectivity of 6 Ewing sarcoma cell lines as compared to other pediatric solid tumor cell lines (FIG. 2A), and 89-fold selectivity for a distinct set of 6 Ewing sarcoma cell lines as compared to 6 rhabdomyosarcoma cell lines (FIG. 2B). Even the EW-8 Ewing sarcoma cell line that is resistant to PARP1 inhibitors, is highly sensitive to altertoxin II, suggesting different mechanism of action.

TABLE 1

Effects of altertoxin II were evaluated using the SRB assay in 3 Ewing sarcoma cell lines as compared to 4 other pediatric solid tumor cells lines and the $GI_{50}$, the concentration that causes 50% growth inhibition and the TGI, total growth inhibitory concentration was determined.

| Cell Line | Type | $GI_{50}$ (nM) | TGI (nM) |
|---|---|---|---|
| RD-ES | EWS | 14 | 60 |
| SK-ES-1 | EWS | 35 | 151 |
| A673 | EWS | 28 | 139 |
| A204 | RMS | 960 | 1500 |
| D283 | Med | 940 | 1700 |

TABLE 1-continued

Effects of altertoxin II were evaluated using the SRB assay in 3 Ewing sarcoma cell lines as compared to 4 other pediatric solid tumor cells lines and the $GI_{50}$, the concentration that causes 50% growth inhibition and the TGI, total growth inhibitory concentration was determined.

| Cell Line | Type | $GI_{50}$ (nM) | TGI (nM) |
| --- | --- | --- | --- |
| SK-N-BE2 | NB | 1000 | 2000 |
| SH-SY-5Y | NB | 560 | 920 | n ≥ 3 independent experiments.
RMS, rhabdomyosarcoma The;
Med, medulloblastoma;
NB, neuroblastoma.

TABLE 2

The effects of altertoxin II were evaluated in 6 Ewing sarcoma cells lines and 6 rhabdomyosarcoma cells lines and the $IC_{50}$, the concentration that causes 50% inhibition of proliferation were determined using the alamar blue assay.

| Cell line | $IC_{50}$ (µM) |
| --- | --- |
| Ewing Sarcoma | |
| ES-2 | 0.023 ± 0.004 |
| ES-4 | 0.020 ± 0.002 |
| ES-7 | 0.003 ± 0.001 |
| ES-8 | 0.007 ± 0.001 |
| EW-8 | 0.0065 ± 0.0003 |
| TC-71 | 0.0046 ± 0.0005 |
| Rhabdomyosarcoma | |
| Rh5 | 1.05 ± 0.23 |
| Rh18 | 0.99 ± 0.12 |
| Rh28 | 0.79 ± 0.09 |
| Rh30 | 0.75 ± 0.06 |
| Rh36 | 1.03 ± 0.21 |
| Rh41 | 1.13 ± 0.30 |

N = 3-6.

The ability of altertoxin II to initiate cell death via apoptosis, as measured by PARP cleavage, was evaluated in two Ewing sarcoma cells lines, SK-ES-1 and RD-ES. The results show that 100 nM altertoxin Ii causes the appearance of cleaved PARP by 7 and 17 hours in SK-ES-1 cells and by 17 hours in RD-ES cells (FIG. 4A). A range of altertoxin II concentrations when then evaluated in SK-ES-1 Ewing sarcoma cells as compared to A204 rhabdomyosarcoma cells. The results, FIG. 4B, show that altertoxin II at both the 100 nM and 1 µM concentration cause apoptosis in the Ewing sarcoma cells but not the rhabdomyosarcoma cells (FIG. 4B).

The effects of altertoxin II on cell cycle distribution were evaluated in 4 Ewing sarcoma cell lines using flow cytometry. Concentration-dependent S-phase arrest was observed in each line, including SK-ES-1 cells (FIG. 5).

An experiment was designed to evaluate whether the effects of altertoxin II in Ewing sarcoma cells required cell cycle transition. RD-ES cells were arrested in the $G_1$ phase of the cell cycle using the CDK4/6 inhibitor LSN2813542. LSN2813542 (100 nM) had no effect on RD-ES cell viability, but caused greater than 85% of the cells to arrest in $G_1$ for at least 48 h. The arrested cells were then treated with altertoxin II and a concentration-response curve generated. The results showed that $G_1$ arrest caused a rightward shift of the concentration-response curve (FIG. 6) as indicated by a 28-fold increase in the total growth inhibition concentration (TGI). These results demonstrate that cell cycle progression is necessary for the potent effects of altertoxin II in Ewing sarcoma cells.

Studies were conducted to test whether altertoxin II initiates DNA damage in Ewing sarcoma cells because of the well-known sensitivity of these cells to DNA damage and prior reports of altertoxin II-induced DNA damage in other mammalian cells (Fleck, S. C. et al., *Toxicol Lett*, 214, 27-32, 2012). The results show that 100 nM altertoxin II rapidly induced H2AX serine 139 phosphorylation (γH2AX) in A673 Ewing sacroma cells (FIG. 7A) within 6 h. High-content imaging of A673 and Rh30 rhabdomyosacroma cells show that 30 nM altertoxin II caused an increase in γH2AX in A673 cells (FIG. 7B). In contrast, no γH2AX foci were detected in Rh30 rhabdomyosacroma cells with altertoxin II concentrations up to 1 µM at either 6 or 24 h. A 10 µM concentration of altertoxin II did initiate γH2AX foci in Rh30 cells after a 24 h exposure, consistent with the relative resistance of these cells to altertoxin II. Consistent with these measures of DNA damage altertoxin II.

The ability of altertoxin II to initiate the formation of 53BP1 foci, another measure of DNA damage, was evaluated in A673 Ewing sarcoma cells and nuclear foci were noted within 6 h at 10 nM and 100 nM concentrations of altertoxin II (FIG. 8A). Multiple investigators have shown that Ewing sarcoma cells undergo replication stress and R-loop accumulation. Based on these results, the ability of altertoxin II to induce R-loops in Ewing sarcoma cells was evaluated. The R-loop marker S9.6 was evaluated in altertoxin II-treated TC-32 cells by immunofluorescence techniques and the results showed that altertoxin II increased formation of R-loops in TC-32 nuclei (FIG. 8B). These results suggest that altertoxin induces replication stress, leading to formation of R-loops.

Downstream activation of DNA damage response proteins by altertoxin II was subsequently evaluated. In A673 and RD-ES Ewing sarcoma cells (FIG. 9A) altertoxin II at concentrations of 10-300 nM, caused phosphorylation of checkpoint kinase 1 and 2 (Chk1 and Chk2) within 6 h. Chk1 phosphorylation was also observed in SK-ES-1 Ewing sarcoma cells treated for 24 h with altertoxin II concentrations of 100 nM and 1 µM, but Chk1 phosphorylation was not observed in A204 rhabdomyosarcoma cells, which are not sensitive to altertoxin II, at concentrations up to 1 µM (FIG. 9B). The phosphorylation of p53, another indication of DNA damage was also observed in RD-ES cells (FIG. 9A). These data together suggest that low concentrations of altertoxin II cause rapid DNA damage, initiate replication stress with S-phase accumulation and an ATR/CHK1 DNA damage response in multiple Ewing sarcoma cell lines and this likely contributes to the exquisite sensitivity of these cells to altertoxin II.

Cellular metabolism leading to the loss of altertoxin II is a possible difference between the altertoxin II sensitive Ewing sarcoma cells and resistant rhabdomyosarcoma cells. Fleck and colleagues demonstrated that mammalian cell lines metabolize ATXII at different rates (Fleck, S. et al., *Chem Res Toxicol*, 27, 247-53, 2014).

An experiment was conducted to test this possibility. TC-32 Ewing sarcoma and Rh30 rhabdomyosarcoma cells were treated with 100 nM ATX for 6 h and the conditioned media was then applied to the resistant Rh30 cells. The results show that the media from altertoxin II-treated TC-32 cells showed substantially higher activity against these normally altertoxin II-resistant cells (FIG. 10), suggesting the possibility that TC-32 cells metabolize altertoxin II slower than Rh30 cells. Differences in the altertoxin II concentration were measured by LC/MS in media from TC-32 and HepG2 hepatocellular carcinoma cells. After 2 h, approximately 25% of the altertoxin II remained in the TC-32 media, but no altertoxin II was detectable in the HepG2 media. These results suggest that TC-32 cells, and potentially other Ewing sarcoma cell lines, do not metabolize altertoxin II as efficiently as other cells which might contribute to their sensitivity.

Studies were conducted to evaluate the in vivo efficacy of altertoxin II in an A673 Ewing sarcoma murine xenograft model (FIG. 11). Mice bearing A673 xenograft tumors were treated with 20 mg/kg altertoxin II on days 1, 3, 5, 8 and 10, or with 40 mg/kg altertoxin II on days 1, 3 and 5. The 40 mg/kg dose of altertoxin II caused in significant inhibition of tumor growth over the 14-day trial. On day 14, tumors in mice in the 40 mg/kg altertoxin II group were significantly smaller than control tumors ($p=0.0001$). Mice treated with the 20 mg/kg dose of altertoxin II showed a trend of modest tumor growth inhibition, but on day 14 no statistically significant difference in tumor volume was observed compared to the control group. These results show that altertoxin II has antitumor efficacy against this A673 Ewing sarcoma xenograft with an acceptable therapeutic window, and that altertoxin II has potential for the treatment of Ewing sarcoma.

General Experimental Procedures: Optical rotation data were recorded on a Rudolph Research AUTOPOL III automatic polarimeter. Varian VNMR spectrometer (400 MHz for $^1$H NMR and 100 MHz for $^{13}$C NMR) was used for collecting the NMR data. LC-ESI(+/−)-MS data were recorded on a Shimadzu LCMS-2020 system (ESI quadrupole) attached with Phenomenex Kintex column (2.6 μm $C_{18}$ column, 100 Å, 75×3.0 mm) and a photodiode array detector. HPLC purifications were performed on a Shimadzu HPLC system with SCL-10A VP system controller coupled with SPD-10A VP UV-VIS detector. Solvents used were either of ACS (for extraction and vacuum liquid chromatography) or HPLC (for HPLC) grade.

Fungal Strain Extraction and Isolation: The fungal culture on cheerios was extracted with ethyl acetate (3×2.5 L) and combined solvent was evaporated to dryness in vaccuo to produce fungal crude extract (FIG. 1 (fraction A), 24.0 g). The deep red extract was fractionated over silica gel vacuum liquid chromatography (VLC) into three sub-fractions by successive elution with dichloromethane (FIG. 1 (fraction B)), 10:1 dichloromethane:methanol (FIG. 1 (fraction C)) and methanol (FIG. 1D). Fraction C was further fractionated through dianion HP-20SS resin VLC to generate six sub-fractions (FIG. 1 (fractions E-J)) eluting with increasing percentage of methanol in water (30%, 50%, 70%, 90% and 100%) followed by a column wash with 50:50 dichloromethane:methanol. Fraction I was subjected to preparative HPLC (Gemini 5 μm $C_{18}$ column, 110 Å, 250×21.2 mm, flow rate 10 mL/min) with gradient elution of MeOH—H$_2$O (0 min, 70% MeOH; 15 min, 100% MeOH, 28 min, 100% MeOH) to generate four sub-fractions (FIG. 1 (fractions K-N)), among which sub-fraction L was further purified over same preparative HPLC column with isocratic elution (60:40 MeCN:H$_2$O) to obtain pure altertoxin II (7.4 mg, yield 0.03%). $^1$H, $^{13}$C NMR, ESI(+)-MS and specific rotation data were in well agreement with the previous studies (Hradil et al., *Phytochemistry* 1989, 28(1):73-75; Schwarz et al., *Arch. Toxicol.* 2012, 86(12):1911-25; Stack et al., *J. Nat. Prod.* 1986, 49(5):866-71). This isolation protocol has been represented schematically in FIG. 1.

The invention claimed is:

1. A method for treating a Ewing sarcoma family tumor (EFT) comprising administering an effective amount of altertoxin II to a subject having a EFT.

2. The method of claim 1, wherein the altertoxin II is a pharmaceutically acceptable salt.

3. The method of claim 1, wherein the subject is a human subject.

4. The method of claim 3, wherein the human subject is a pediatric subject.

5. The method of claim 1, wherein the effective amount of altertoxin II is between 1 mg and 500 mg.

6. The method of claim 1, further comprising administering a chemotherapy, radiotherapy, or immunotherapy.

7. The method of claim 1, wherein the EFT is a Ewing sarcoma.

8. The method of claim 1, wherein altertoxin II is administer orally or by injection.

9. The method of claim 8, wherein administering by injection is by intravenous injection.

10. The method of claim 8, wherein administering by injection is by local injection.

* * * * *